(12) United States Patent
Jan et al.

(10) Patent No.: US 6,388,159 B1
(45) Date of Patent: May 14, 2002

(54) XYLENE ISOMERIZATION PROCESS USING UZM-5 AND UZM-6 ZEOLITES

(75) Inventors: Deng-Yang Jan, Elk Grove Village; Gregory J. Lewis; Jaime G. Moscoso, both of Mt. Prospect; Mark A. Miller, Niles; Qianjun Chen, Des Plaines, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/705,839

(22) Filed: Nov. 3, 2000

(51) Int. Cl.⁷ .................................................. C07C 5/22
(52) U.S. Cl. ....................... 585/481; 585/482
(58) Field of Search ................... 585/480, 481, 585/482; 502/66, 74; 423/781, 705, 708

(56) References Cited

U.S. PATENT DOCUMENTS 5,202,014 A * 4/1993 Zones et al. .................. 208/46

* cited by examiner

*Primary Examiner*—Thuan D. Dang
(74) *Attorney, Agent, or Firm*—John G. Tolomei; Frank S. Molinaro

(57) ABSTRACT

A process for isomerising xylene using a new family of related crystalline aluminosilicate zeolites has been developed. These zeolites are represented by the empirical formula:

$$M_m^{n+}R_r^{p+}Al_{(1-x)}E_xSi_yO_z$$

where M is an alkali or alkaline earth metal such as lithium and strontium, R is a nitrogen containing organic cation such as tetramethyl-ammonium and E is a framework element such as gallium.

19 Claims, No Drawings

XYLENE ISOMERIZATION PROCESS USING UZM-5 AND UZM-6 ZEOLITES

FIELD OF THE INVENTION

This invention relates to a process for isomerizing xylenes using a family of related crystalline aluminosilicate zeolites examples of which have been designated UZM-5, UZM-5P and UZM-6. These compositions are structurally different from other known zeolites.

BACKGROUND OF THE INVENTION

Zeolites are crystalline aluminosilicate compositions which are microporous and which have a three-dimensional oxide framework formed from corner sharing $AlO_2$ and $SiO_2$ tetrahedra. Numerous zeolites, both naturally occurring and synthetically prepared are used in various industrial processes such as hydrocarbon conversion processes. One particular process which uses zeolites as a catlyst is the isomerization of aromatic compounds, especially the isomerization of $C_8$ aromatic compounds. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalyst composite and process which enhance conversion according to the latter approach, i.e., achieve ethylbenzene isomerization to xylenes with high conversion, would effect significant improvements in xylene-production economics.

Applicants have synthesized a family of crystalline zeolitic compositions which have unique x-ray diffraction patterns and have the empirical formula on an anhydrous basis in terms of molar ratios of:

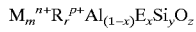

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of quaternary ammonium ions, protonated amines, protonated diamines, protonated alkanolamines, quaternary alkanolammonium ions and diquaternary ammonium ions, and mixtures thereof, "r" is the mole ratio of R to (Al+E) and has a value of about 0.25 to about 3.0, E is an element selected from the group consisting of Ga, Fe, Cr, In and B, "x" is the mole fraction of E and varies from 0 to about 0.5, "n" is the weighted average valence of M and has a value of +1 to about +2, "p" is the weighted average valence of R and has a value of +1 to about +2, "y" is the mole ratio of Si to (Al+E) and varies from about 5 to about 12. and "z" is the mole ratio of O to (Al+E) and has a value determined by the equation:

$$z=(m·n+r·p+3+4·y)/2.$$

Specific members of this family of zeolites are: UZM-5, UZM-5P and UZM-6.

SUMMARY OF THE INVENTION

This invention relates to a process for isomerizing aromatic compounds using a new family of zeolites. Accordingly, one embodiment of the invention is a process for the isomerization of a non-equilibrium feed mixture of xylenes and ethylbenzene comprising contacting the feed mixture in the presence of hydrogen in an isomerization zone with a catalyst composite comprising an effective amount of at least one platinum-group metal component and an aluminosilicate crystalline zeolite at isomerization conditions to obtain an isomerized product comprising a higher proportion of p-xylene than in the feed mixture, the zeolite having a composition in the as synthesized form in terms of mole ratios of the elements given by:

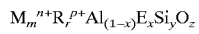

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is at least one element selected from the group consisting of Ga, Fe, Cr, In and B, "X" is the mole fraction of E and varies from 0 to 0.5, "n" is the weighted average valence of M and has a value of about +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$$z=(m·n+r·p+3+4·y)/2$$

the material characterized in that it has at least two x-ray diffraction peaks, one at a d-spacing of 3.9±0.12 Å and one at 8.6±0.2 Å.

Isomerization conditions comprise a temperature of about 1000 to about 500° C., a pressure of about 1 to about 50 atmospheres, a liquid hourly space velocity from about 0.5 to 10 $hr^{-1}$ and a hydrogen-to-hydrocarbon mole ratio from about 0.5:1 to 25:1.

In a particular embodiment, the zeolite catalyst has been designated UZM-5 and has the x-ray diffraction pattern having at least the d-spacings and intensities set forth in Table A:

TABLE A

UZM-5

| 2-θ | d(Å) | I/I₀% |
|---|---|---|
| 6.31–5.89 | 14.00–15.00 | w-m |
| 7.96–7.58 | 11.10–11.65 | m-s |
| 10.40–10.01 | 8.50–8.83 | w-m |
| 12.11–11.59 | 7.30–7.63 | m |
| 16.10–15.53 | 5.50–5.70 | m-vs |
| 19.28–18.55 | 4.60–4.78 | w-m |
| 22.26–21.60 | 3.99–4.11 | m |
| 23.20–22.43 | 3.83–3.96 | w-s |
| 24.16–23.33 | 3.68–3.81 | vs |
| 30.48–29.55 | 2.93–3.02 | w-m |
| 31.94–30.92 | 2.80–2.89 | w-m |
| 44.83–43.47 | 2.02–2.08 | w |

This and other objects and embodiments will become more apparent after the following detailed description of the invention.

DETAILED DESCRIPTION OF THE INVENTION

One essential aspect of the process of the invention is a new family of zeolites. Three species have been designated UZM-5, UZM-5P and UZM-6. In its as-synthesized form, these zeolites have a composition on an anhydrous basis that is represented by the formula:

$$M_m^{n+}R_r^{p+}Al_{(1-x)}E_xSi_yO_z.$$

M is an exchangeable cation and is selected from the group consisting of alkali and alkaline earth metals. Specific examples of the M cations include but are not limited to lithium, sodium, potassium, cesium, strontium, calcium, magnesium, barium and mixtures thereof. The value of "m" which is the mole ratio of M to (Al+E) varies from 0 to 1.2. R is a nitrogen containing organic cation and is selected from the group consisting of protonated amines, protonated diamines, protonated alkanolamines, quaternary ammonium ions, diquaternary ammonium ions, quaternized alkanolammonium ions and mixtures thereof. The value of "r" which is the mole ratio of R to (Al+E) and varies from about 0.25 to about 3.0. The value of "n" which is the weighted average valence of M varies from +1 to about +2. The value of "p", which is the average weighted valence of the organic cation has a value from about +1 to about +2. E is an element which is present in the framework and is selected from the group consisting of gallium, iron, boron, chromium, indium and mixtures thereof. The value of "x" which is the mole fraction of E varies from 0 to about 0.5. The ratio of silicon to (Al+E) is represented by "y" which varies from about 5 to about 12, while the mole ratio of O to (Al+E) is represented by "z" and has a value given by the equation:

$$z=(m \cdot n+r \cdot p+3+4 \cdot y)/2.$$

When M is only one metal, then the weighted average valence is the valence of that one metal, i.e. +1 or +2. However, when more than one M metal is present, the total amount of:

$$M_m^{n+}=M_{m1}^{(n1)+}+M_{m2}^{(n2)+}+M_{m3}^{(n3)+}+\ldots$$

and the weighted average valence "n" is given by the equation:

$$n = \frac{m_1 \cdot n_1 + m_2 \cdot n_2 + m_3 \cdot n_3 + \cdots}{m_1 + m_2 + m_3 \cdots}$$

Similarly when only one R organic cation is present, the weighted average valence is the valence of the single R cation, i.e., +1 or +2. When more than one R cation is present, the total amount of R is given by the equation:

$$R_r^{p+}=R_{r1}^{(p1)+}+R_{r2}^{(p2)+}+R_{r3}^{(p3)+}$$

and the weighted average valence "p" is given by the equation:

$$p = \frac{p_1 \cdot r_1 + p_2 \cdot r_2 + p_3 \cdot r_3 + \cdots}{r_1 + r_2 + r_3 + \cdots}.$$

These aluminosilicate zeolites are prepared by a hydrothermal crystallization of a reaction mixture prepared by combining reactive sources of R, aluminum, silicon and optionally E and/or M in aqueous media. Accordingly, the aluminum sources include, but are not limited to, aluminum alkoxides, precipitated alumina, aluminum hydroxide, aluminum salt and aluminum metal. Specific examples of aluminum alkoxides include, but are not limited to aluminum ortho sec-butoxide, and aluminum orthoisopropoxide. Sources of silica include but are not limited to tetraethylorthosilicate, fumed silicas, precipitated silicas and colloidal silica. Sources of the M metals include the halide salts, nitrate salts, acetate salts, and hydroxides of the respective alkali or alkaline earth metals. Sources of the E elements include but are not limited to alkali borates, boric acid, precipitated gallium oxyhydroxide, gallium sulfate, ferric sulfate, ferric chloride, chromium chloride, chromium nitrate, indium chloride and indium nitrate. When R is a quaternary ammonium cation, the sources include without limitation the hydroxide, and halide compounds. Specific examples include without limitation tetramethylammonium hydroxide, tetraethylammonium hydroxide, hexamethonium bromide, tetramethylammonium chloride, methyltriethylammonium hydroxide. R may also be neutral amines, diamines, and alkanolamines. Specific examples are triethanolamine, triethylamine, and N,N,N',N'tetramethyl-1,6-hexanediamine.

The reaction mixture containing reactive sources of the desired components can be described in terms of molar ratios of the oxides by the formula:

$$aM_{2/n}O:bR_{2/p}O:(1-c)Al_2O_3: cE_2O_3:dSiO_2:eH_2O$$

where "a" is the mole ratio of the oxide of M and has a value from 0 to about 2, "b" is the mole ratio of the oxide of R and has a value of about 1.5 to about 30, "d" is the mole ratio of silica and has a value of about 5 to about 30, "c" is the mole ratio of the oxide of E and has a value from 0 to about 0.5, and "e" is the mole ratio of water and has a value of about 30 to about 6000. The reaction mixture is now reacted at a temperature of about 100° C. to about 175° C. and preferably from about 140° C. to about 160° C. for a period of about 12 hours to about 14 days and preferably for a time of about 2 days to about 5 days in a sealed reaction vessel under autogenous pressure. After crystallization is complete, the solid product is isolated from the heterogeneous mixture by means such as filtration or centrifugation, and then washed with de-ionized water and dried in air at ambient temperature up to about 100° C.

As synthesized, the zeolites will contain some of the exchangeable or charge balancing cations in its pores. These exchangeable cations can be exchanged for other cations, or in the case of organic cations, they can be removed by heating under controlled conditions. All of these methods are well known in the art.

The crystalline silicoalumino zeolites are characterized by a three-dimensional framework structure of at least $SiO_2$ and $AlO_2$ tetrahedral units. These zeolites are further characterized by their unique x-ray diffraction pattern. The x-ray diffraction pattern has at least two peaks: one peak at a d-spacing of about 3.9±0.12 Å and one peak at a d-spacing of about 8.6±0.20 Å. To allow for ready reference, the different structure types and compositions of crystalline zeolites have been given arbitrary designation of UZM-h, where "h" is an integer starting at one and where for example "1" represents a framework of structure type "1". That is one or more zeolitic composition with different empirical formulas can have the same structure type "h", e.g. "1".

In this respect, the following species can be identified by their x-ray diffraction patterns which have at least the d-spacing and relative intensities set forth in Tables A to C.

TABLE A

| UZM-5 | | |
|---|---|---|
| 2-θ | d(Å) | $I/I_o$% |
| 6.31–5.89 | 14.00–15.00 | w-m |
| 7.96–7.58 | 11.10–11.65 | m-s |
| 10.40–10.01 | 8.50–8.83 | w-m |
| 12.11–11.59 | 7.30–7.63 | m |
| 16.10–15.53 | 5.50–5.70 | m-vs |
| 19.28–18.55 | 4.60–4.78 | w-m |
| 22.26–21.60 | 3.99–4.11 | m |
| 23.20–22.43 | 3.83–3.96 | w-s |
| 24.16–23.33 | 3.68–3.81 | vs |
| 30.48–29.55 | 2.93–3.02 | w-m |
| 31.94–30.92 | 2.80–2.89 | w-m |
| 44.83–43.47 | 2.02–2.08 | w |

TABLE B

| UZM-5P | | |
|---|---|---|
| 2-θ | d(Å) | $I/I_o$% |
| 6.31–5.19 | 14.00–17.00 | w-vs |
| 7.96–7.56 | 11.10–11.70 | w-m |
| 10.52–10.04 | 8.40–8.80 | m-s |
| 16.56–15.67 | 5.35–5.65 | w-m |
| 19.49–18.87 | 4.55–4.70 | w-m |
| 23.52–22.09 | 3.78–4.02 | w-vs |
| 24.03–23.39 | 3.70–3.80 | w-vs |
| 30.81–29.76 | 2.90–3.00 | w-m |
| 31.94–30.81 | 2.80–2.90 | w-m |
| 45.30–43.04 | 2.00–2.10 | w-m |

TABLE C

| UZM-6 | | |
|---|---|---|
| 2-θ | d(Å) | $I/I_o$% |
| 6.31–5.89 | 14.00–15.00 | w-m |
| 7.96–7.58 | 11.10–11.65 | m-s |
| 10.40–10.01 | 8.50–8.83 | w-m |
| 12.11–11.59 | 7.30–7.63 | m |
| 16.10–15.53 | 5.50–5.70 | m-vs |
| 19.28–18.55 | 4.60–4.78 | w-m |
| 22.26–21.60 | 3.99–4.11 | m |
| 23.20–22.43 | 3.92–4.00 | m-vs |

TABLE C-continued

| UZM-6 | | |
|---|---|---|
| 2-θ | d(Å) | $I/I_o$% |
| 24.16–23.33 | 3.83–3.96 | w-s |
| 30.48–29.55 | 3.68–3.81 | s-vs |
| 31.94–30.92 | 2.80–2.89 | m |
| 44.83–43.47 | 2.02–2.08 | w |

The zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 $m^2/g$, and relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50–200° C. and subjected to a calcination procedure at a temperature of about 450–700° C. for a period of about 1 to about 20 hours. This treatment effects conversion of the hydrogel to the corresponding alumina matrix.

A platinum-group metal, including one or more of platinum, palladium, rhodium, ruthenium, osmium, and iridium, is an essential component of the present catalyst. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. The platinum-group metal component generally comprises from about 0.01 to about 5 mass-% and preferably from about 0.1 to about 2% of the final catalyst composite, calculated on an elemental basis.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the zeolite and binder. Yet another method of effecting a suitable metal distribution is by compositing the metal component with the binder prior to co-extruding the zeolite and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like.

It is within the scope of the present invention that the catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst composite of the present invention may contain a halogen component. The halogen component may be either fluorine, chlorine, bromine or iodine or mixtures thereof, with chlorine being preferred. The halogen component is generally present in a combined state with the inorganic-oxide support. The optional halogen component is preferably well dispersed throughout the catalyst and may comprise from more than 0.2 to about 15 wt. %, calculated on an elemental basis, of the final catalyst. The halogen component may be incorporated in the catalyst composite in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and, usually, calcined at a temperature of from 400° about 650° C. in an air atmosphere for a period of from about 1 to about 10 hours until the metallic compounds present are converted substantially to the oxide form. If desired, the optional halogen component may be adjusted by including a halogen or halogen-containing compound in the air atmosphere.

The resultant calcined composite optimally is subjected to a substantially water-free reduction step to insure a uniform and finely divided dispersion of the optional metallic components. The reduction optionally may be effected in situ. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

The feedstock to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include without limitation ortho-xylene, meta-xylene, para-xylene, ethylbenzene, ethyltoluenes, trimethylbenzenes, di-ethylbenzenes, tri-ethyl-benzenes, methylpropylbenzenes, ethylpropylbenzenes, di-isopropylbenzenes, and mixtures thereof.

Isomerization of a $C_8$-aromatic mixture containing ethylbenzene and xylenes is a particularly preferred application for the zeolites of the invention. Generally such mixture will have an ethylbenzene content in the approximate range of 5 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_8$-aromatic isomer is present in a concentration that differs substantially (defined herein as a difference of at least 5 mass-% of the total $C_8$ aromatics) from the thermodynamic equilibrium concentration of that isomer at isomerization conditions. Usually the non-equilibrium mixture is prepared by removal of para- and/or ortho-xylene from a fresh $C_8$ aromatic mixture obtained from an aromatics-production process, and preferably the non-equilibrium mixture contains less than 5 mass-% para-xylene.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with a catalyst of the type hereinafter described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromaticisomerization conditions. Such conditions comprise a temperature ranging from about 0° to 600° C. or more, and preferably is in the range of from about 100° to 500° C. The pressure generally is from about 1 to 100 atmospheres absolute, preferably less than about 50 atmospheres. Sufficient catalyst is contained in the isomerization zone to provide a liquid hourly space velocity with respect to the hydrocarbon feed mixture of from about 0.1 to 30 $hr^{-1}$, and preferably 0.5 to 10 $hr^{-1}$. The hydrocarbon feed mixture optimally is reacted in admixture with hydrogen at a hydrogen/hydrocarbon mole ratio of about 0.5:1 to about 25:1 or more. Other inert diluents such as nitrogen, argon and light hydrocarbons may be present.

The reaction proceeds via the mechanism, described hereinabove, of isomerizing xylenes while reacting ethylbenzene to form a xylene mixture via conversion to and reconversion from naphthenes. The yield of xylenes in the product thus is enhanced by forming xylenes from ethylbenzene. The loss of $C_8$ aromatics through the reaction thus is low: typically less than about 4 mass-% per pass of $C_8$ aromatics in the feed to the reactor, preferably about 3 mass-% or less, and most preferably no more than about 2.5 mass-%.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

In order to more fully illustrate the invention, the following examples are set forth. It is to be understood that the examples are only by way of illustration and are not intended as an undue limitation on the broad scope of the invention as set forth in the appended claims.

EXAMPLE 1

An aluminosilicate reaction mixture was prepared in the following manner. Aluminum sec-butoxide (95+%), 58.75 g, was added to 836.34 g TEAOH (35%) with vigorous stirring. To this mixture, 294.73 g colloidal silica, (Ludox AS-40, 40% $SiO_2$) was added, followed by the addition of 10.18 g distilled water. The reaction mixture was homogenized for 1 hr with a high-speed mechanical stirrer, and then aged in teflon bottles overnight at 95° C. After the aging step, the reaction mixture was recombined and analyzed, the analysis indicated a silicon content of 4.67%.

A 500 g portion of this reaction mixture was treated with TMACl solution consisting of 11.77 g TMACl (97%) dissolved in 23.0 g distilled water while applying vigorous mixing. After a half hour of homogenization the reaction mixture was distributed among 8 teflon-lined autoclaves. The autoclaves were all placed in ovens set at 150° C., where the reaction mixtures were digested for 4 days at autogenous pressures. The solid products were recovered by centrifugation, washed, and dried at 95° C.

The composition of the isolated product consisted of the mole ratios Si/Al=6.88, N/Al=0.83 and C/N=6.05. Scanning Electron Microscopy (SEM) showed the crystallites to consist of clustered platelets approximately 100–300 nm across. Characterization by powder X-ray diffraction (XRD) showed the lines in the pattern to be those for the new material designated UZM-5. Table 1 below shows lines characteristic of the phase. A portion of the sample was calcined byramping to 540° C. at 2° C./min in $N_2$, holding at 540° C. in $N_2$ for 1 hr followed by 7 hr dwell in air, also at 540° C. The BET surface area was found to be 530 $m^2/g$, and the micropore volume was 0.2 cc/g.

TABLE 1

| 2-θ | d(Å) | $I/I_o$% |
| --- | --- | --- |
| 6.24 | 14.15 | m |
| 7.90 | 11.18 | m |
| 10.32 | 8.57 | w-m |
| 12.00 | 7.37 | m |
| 15.80 | 5.60 | m-s |
| 16.34 | 5.42 | m |
| 19.05 | 4.66 | w-m |
| 22.00 | 4.04 | m |
| 22.86 | 3.89 | m |
| 23.80 | 3.74 | vs |
| 27.40 | 3.25 | w |
| 30.14 | 2.96 | w |
| 30.90 | 2.89 | w |
| 31.60 | 2.83 | m |
| 33.20 | 2.70 | w |
| 34.56 | 2.59 | w |
| 36.64 | 2.45 | w |
| 44.32 | 2.04 | w |

EXAMPLE 2

An aluminosilicate reaction mixture was prepared by adding 197.31 g Al(Osec-Bu)$_3$ to 2808.74 g TEAOH (35%), followed by the addition of 989.82 g colloidal silica (Ludox AS-40) while maintaining vigorous stirring. The reaction mixture was aged at 95° C. for 16 hr and then allowed to cool. This aluminosilicate reaction mixture was designated Mixture A. Elemental analysis showed Mixture A to contain 4.79% Si. A portion of Mixture A, 110 g, was placed in a teflon beaker equipped with a high-speed stirrer. Separately, a solution was prepared by dissolving 1.27 g TMACl (97%) and 0.68 g NaCl in 6 g de-ionized water. This solution was added to the stirring aluminosilicate reaction mixture. After a half-hour of homogenization, the reaction mixture was divided among 4 teflon-lined autoclaves which were digested under a variety of conditions. The solid products were isolated by filtration, washed with de-ionized water, and dried at 95° C.

The products of all of the reactions exhibited the x-ray diffraction pattern of UZM-5. Characteristic lines in the x-ray diffraction pattern of a sample digested for 150° C. for 4 days are shown in Table 2. Scanning Electron Microscopy showed the sample to be very uniform, consisting of rosettes of plate-like crystals from about 0.5 to about 2 $\mu$ across. The BET surface area for this material was found to be 553 m$^2$/g, while the micropore volume was 0.22 cc/g. Elemental analysis showed the Si/Al ratio to be 5.97, Na/Al=0.19, N/Al=0.97, and C/N=5.59.

TABLE 2

| 2-θ | d(Å) | I/I$_o$% |
|---|---|---|
| 6.16 | 14.33 | m |
| 7.76 | 11.39 | s |
| 10.12 | 8.73 | m |
| 11.82 | 7.48 | m |
| 15.74 | 5.63 | vs |
| 19.04 | 4.66 | m |
| 20.36 | 4.36 | w |
| 21.84 | 4.07 | m |
| 22.68 | 3.92 | s |
| 23.56 | 3.77 | vs |
| 26.18 | 3.40 | w |
| 27.02 | 3.30 | m |
| 29.98 | 2.98 | m |
| 31.32 | 2.85 | m |
| 33.12 | 2.70 | m |
| 44.10 | 2.05 | w |

EXAMPLE 3

An aluminosilicate reaction mixture was prepared in the following manner: Al(Osec-Bu)$_3$ (95+%), 116.09 g, was added to 1983.17 g TEAOH (35%) and 1.86 g de-ionized water with vigorous stirring. Then 698.88 g Ludox AS-40 was added with continued stirring. After an hour of homogenization, the aluminosilicate reaction mixture was placed in several teflon bottle and aged at 95° C. for 3 days. After the aging process, elemental analysis showed the mixture to contain 5.01% Si and had a Si/Al ratio of 10.03. This reaction mixture was designated Mixture B. A portion of Mixture B, 40.0 g, was placed in a beaker where it was stirred vigorously. Separately, 0.78 g TMACl (97%) was dissolved in 15.0 g de-ionized water. This solution was added to the stirring aluminosilicate reaction mixture in a dropwise fashion. The mixture was allowed to homogenize further for about an hour. The reaction mixture was then placed in a teflon-lined autoclave and digested at 150° C. for 6 days at autogenous pressures. The solid product was isolated by centrifugation, washed with de-ionized water, and dried at 95° C.

The product had a x-ray pattern which corresponded to a new zeolite and the zeolite was designated UZM-6. Scanning Electron Microscopy (SEM) showed the material to consist of plate-like crystals about 0.1–0.4 $\mu$ across and less than 0.05 $\mu$ thick. The Si/Al ratio of the product UZM-6 was 8.34 by elemental analysis. The BET surface area of the sample was 520 m$^2$/g, with a micropore volume of 0.21 cc/g. Characteristic lines in the x-ray diffraction pattern are given in Table 3.

TABLE 3

| 2-θ | d(Å) | I/I$_o$% |
|---|---|---|
| 6.14 | 14.38 | m |
| 7.76 | 11.38 | m |
| 10.12 | 8.73 | m |
| 11.82 | 7.48 | m |
| 15.68 | 5.65 | s |
| 16.30 | 5.43 | m |
| 18.98 | 4.67 | m |
| 20.32 | 4.37 | w |
| 21.86 | 4.06 | m |
| 22.42 | 3.96 | s |
| 22.78 | 3.90 | m |
| 23.68 | 3.75 | vs |
| 25.24 | 3.53 | w |
| 26.28 | 3.39 | w |
| 26.88 | 3.31 | m |
| 27.34 | 3.26 | m |
| 29.64 | 3.01 | m |
| 30.08 | 2.97 | w |
| 31.44 | 2.84 | w |
| 33.20 | 2.70 | w |
| 44.14 | 2.05 | w |

EXAMPLE 4

An aluminosilicate reaction mixture was prepared in an identical manner to Mixture B described in example 3. However, the reaction mixture was determined to be slightly different by analysis, with a Si content of 4.79 wt % and a Si/Al ratio of 9.59. A portion of this aluminosilicate reaction mixture, 1100 g, was placed in a large beaker equipped with a high-speed stirrer. Separately, a solution was prepared by dissolving 4.14 g LiCl and 21.43 g TMACl (97%) in 65 g de-ionized water. This solution was added dropwise to the aluminosilicate reaction mixture with stirring and was homogenized for an hour. The reaction mixture was then transferred to a static 2-L Parr reactor and digested at 150° C. for 3 days at autogenous pressure. The solid product was isolated by filtration, washed with de-ionized water and dried at 95° C.

Powder x-ray diffraction on a sample of the product showed the pattern to be consistent with that known for UZM-6. The Si/Al ratio was 7.58. The BET surface area was 512 m$^2$/g, while the micropore volume was found to be 0.18 cc/g. SEM of the calcined product showed it to consist of bent plate crystals, sometimes stacked, up to 0.1–0.4 $\mu$ across and less that 0.05 $\mu$ thick. Characteristic lines in the x-ray diffraction pattern are given in Table 4.

TABLE 4

| 2-θ | d(Å) | I/I$_o$% |
|---|---|---|
| 6.28 | 14.07 | m |
| 7.84 | 11.27 | s |
| 10.22 | 8.65 | m |
| 11.92 | 7.42 | m |
| 15.93 | 5.56 | m |
| 18.98 | 4.67 | m |
| 21.98 | 4.04 | w |
| 22.52 | 3.95 | vs |
| 22.92 | 3.88 | m |
| 23.76 | 3.74 | vs |
| 26.33 | 3.38 | w |
| 26.92 | 3.31 | m |
| 31.36 | 2.85 | m |
| 33.26 | 2.69 | m |
| 44.24 | 2.05 | w |

EXAMPLE 5

The zeolites disclosed here were tested for xylene isomerization. The materials were converted to an acid form before testing. Material isolated from the procedure of example 1 was tested after calcination at 550° C. in air for 5 hr. This sample was designated UZM-5, Ex.1. A portion of the same material was acid washed (9 g sample, 2 g H₂SO₄ (98%) in 60 g de-ionized water, 90° C., 2 hr), washed with water, and ammonium ion exchanged (1 N NH₄Cl, 90° C., 1.5 hr) before calcination at 550° C. for 5 hr. This sample was designated UZM-5, Ex.1-AW. The material from example 2 was calcined at 5500° C. for 5 hr, ammonium ion exchanged 3 times (1 N NH₄Cl, 75° C.), and calcined at 550° C. for 2 hr. This sample was designated UZM-5, Ex. 2. The UZM-6 from example 3 was calcined in N₂ for 1 hr and 19 hr in air at 520° C. and was designated UZM-6, Ex. 3. The UZM-6 from example 4 was obtained in a proton form by calcination at 350° C. for 1.5 hr, then 450° C. for 1.5 hr, and 580° C. for 1 hr in N₂, followed by 6 hr calcination in air. Then 85 g of the calcined material was exchanged in 2L of 10% NH₄Cl solution at 80° C. for 2 hr, which was repeated 3 times. Finally, the sample was calcined for 2 hr at 500° C. in air. This sample was designated UZM-6, Ex. 4. For microreactor testing, the samples were sized to 40–60 mesh and activated in a muffle furnace in a flow of air at 550° C. for 2 hr. The meshed samples, 125 mg, were loaded into an 11 mm i.d. quartz reactor sitting in a furnace; the outlet of the reactor was at atmospheric pressure. The samples were preheated to 375° C. in a flow of H₂. The flow of H₂ was then directed through a saturator, where it was saturated with either m-xylene or o-xylene at 0° C. The flow of H₂ was controlled at 50 cc/min. The furnace was then stepped through temperatures of 375° C., 400° C., 425° C., 450° C., 475° C., and 425° C. Product effluents at each temperature were directed to an on-line GC to obtain activity and selectivity measurements. The results from m-xylene and o-xylene isomerization are shown in Tables 5a and 5b, respectively.

TABLE 5A m-Xylene Isomerization Data.

| m-xylene isomerization | UZM-5, Ex. 1 | | | UZM-5, Ex. 1-AW | | |
|---|---|---|---|---|---|---|
| Temperature (deg C.) | 375 | 425 | 475 | 375 | 425 | 475 |
| Flow Rate (cc/min) | 50 | 50 | 50 | 50 | 50 | 50 |
| Methane | 0.05 | 0.21 | 0.23 | 0.17 | 0.22 | 0.21 |
| Benzene | 0.09 | 0.09 | 0.1 | 0.1 | 0.1 | 0.1 |
| Toluene | 0.78 | 0.57 | 0.51 | 1.18 | 0.9 | 0.92 |
| Ethylbenzene | 0 | 0 | 0 | 0 | 0 | 0 |
| p-Xylene | 20.69 | 24.27 | 24.36 | 24.12 | 24.14 | 23.97 |
| m-Xylene | 62.58 | 54.19 | 51.78 | 53.92 | 51.57 | 50.95 |
| o-Xylene | 15.06 | 20.45 | 22.77 | 19.25 | 22.15 | 22.93 |
| 135TMBZ | 0.18 | 0 | 0 | 0.31 | 0.22 | 0.21 |
| 124TMBZ | 0.5 | 0.22 | 0.24 | 0.83 | 0.6 | 0.6 |
| 123TMBZ | 0.07 | 0 | 0 | 0.11 | 0.09 | 0.1 |
| 1235TTMBZ | 0 | 0 | 0 | 0 | 0 | 0 |
| 1234TTMBZ | 0 | 0 | 0 | 0 | 0 | 0 |
| 1245TTMBZ | 0 | 0 | 0 | 0 | 0 | 0 |
| Total Unknowns | 0 | 0 | 0 | 0 | 0 | 0 |
| m-xylene conversion | 37.42 | 45.81 | 48.22 | 46.08 | 48.43 | 49.05 |
| m-xylene isomerization | UZM-6, Ex. 3 | | | UZM-6, Ex. 4 | | |
| Temperature (deg C.) | 375 | 425 | 475 | 375 | 425 | 475 |
| Flow Rate (cc/min) | 50 | 50 | 50 | 50 | 50 | 50 |
| Methane | 0.12 | 0.16 | 0.18 | 0.12 | 0.32 | 0.65 |
| Benzene | 0.12 | 0.1 | 0.12 | 0.14 | 0.12 | 0.22 |
| Toluene | 8.06 | 5.53 | 5.3 | 10.57 | 6.76 | 9.08 |
| Ethylbenzene | 0 | 0 | 0 | 0 | 0 | 0 |
| p-Xylene | 19.85 | 21.31 | 21.49 | 18.41 | 20.7 | 19.21 |
| m-Xylene | 43.21 | 45.63 | 45.56 | 40.01 | 44.27 | 40.89 |
| o-Xylene | 18.09 | 19.89 | 20.55 | 16.81 | 19.33 | 18.51 |
| 135TMBZ | 2.56 | 1.75 | 1.55 | 3.35 | 2.01 | 2.51 |

TABLE 5A-continued m-Xylene Isomerization Data.

| 124TMBZ | 6.57 | 4.67 | 4.33 | 8.55 | 5.37 | 6.97 |
|---|---|---|---|---|---|---|
| 123TMBZ | 0.92 | 0.7 | 0.69 | 1.2 | 0.08 | 1.11 |
| 1235TTMBZ | 0.25 | 0.14 | 0.13 | 0.4 | 0.18 | 0.3 |
| 1234TTMBZ | 0.06 | 0 | 0 | 0.09 | 0 | 0.08 |
| 1245TTMBZ | 0.2 | 0.11 | 0.1 | 0.32 | 0.13 | 0.22 |
| Total Unknowns | 0 | 0 | 0 | 0 | 0 | 0.25 |
| m-xylene conversion | 56.69 | 54.37 | 54.44 | 59.99 | 45.73 | 59.11 |

TABLE 5b o-xylene Isomerization Data.

| o-xylene isomerization | UZM-5, Ex. 1-AW | | | UZM-5, Ex. 2 | | |
|---|---|---|---|---|---|---|
| Temperature (deg C.) | 375 | 425 | 475 | 375 | 425 | 475 |
| Flow Rate (cc/min) | 50 | 50 | 50 | 50 | 50 | 50 |
| METHANE | 0.00 | 0.00 | 0.00 | 0.00 | 0.00 | 0.00 |
| ETHANE | 0.06 | 0.07 | 0.20 | 0.09 | 0.13 | 0.19 |
| PROPANE | 0.00 | 0.00 | 0.00 | 0.00 | 0.00 | 0.00 |
| ETHYLCYCLOHEXANE | 0.11 | 0.10 | 0.07 | 0.11 | 0.09 | 0.00 |
| BENZENE | 0.13 | 0.13 | 0.13 | 0.15 | 0.15 | 0.16 |
| TOLUENE | 0.12 | 0.13 | 0.22 | 0.29 | 0.34 | 0.50 |
| ETHYLBENZENE | 0.00 | 0.00 | 0.00 | 0.12 | 0.11 | 0.10 |
| p-XYLENE | 6.18 | 14.60 | 20.61 | 14.19 | 21.04 | 23.06 |
| m-XYLENE | 30.68 | 43.71 | 49.52 | 45.15 | 50.51 | 51.16 |
| o-XYLENE | 62.55 | 41.06 | 29.00 | 39.52 | 27.19 | 24.09 |
| 135-TM-BENZENE | 0 | 0 | 0 | 0.10 | 0.12 | 0.17 |
| 124-TM-BENZENE | 0 | 0 | 0 | 0.28 | 0.31 | 0.47 |
| 123-TM-BENZENE | 0.13 | 0.19 | 0.25 | 0.00 | 0.00 | 0.08 |
| 1245-TETRAM-BENZ | 0 | 0 | 0 | 0.00 | 0.00 | 0.00 |
| 1235-TETRAM-BENZ | 0 | 0 | 0 | 0.00 | 0.00 | 0.00 |
| 1234-TETRAM-BENZ | 0 | 0 | 0 | 0.00 | 0.00 | 0.00 |
| o-xylene conversion | 37.45 | 58.84 | 71.00 | 60.48 | 72.81 | 75.91 |

We claim as our invention:

1. A process for the isomerization of a non-equilibrium feed mixture comprising xylenes and ethylbenzene comprising contacting the feed mixture in the presence of hydrogen in an isomerization zone with a catalyst composite comprising an effective amount of at least one platinum-group metal component and a crystalline aluminosilicate zeolite at isomerization conditions to obtain an isomerized product comprising a higher proportion of p-xylene than in the feed mixture, the zeolite characterized in that it is a microporous crystalline zeolite having a composition in the as synthesized form on an anhydrous basis in terms of mole ratios of the elements of:

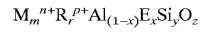

where M is at least one exchangeable cation selected from the group consisting of alkali and alkaline earth metals, "m" is the mole ratio of M to (Al+E) and varies from about 0 to about 1.2, R is a nitrogen-containing organic cation selected from the group consisting of protonated amines, protonated diamines, protonated alkanolamines, quaternary ammonium ions, diquaternaryammonium ions, quaternized alkanolamines and mixtures thereof, "r" is the mole ratio of R to (Al+E) and has a value of about 0.25 to about 3.0, E is at least one element selected from the group consisting of Ga, Fe, Cr, In and B, "X" is the mole fraction of E and varies from 0 to 0.5, "n" is the weighted average valence of M and has a value of about +1 to about +2, "p" is the weighted average valence of R and has a value of +1 to about +2, "y" is the mole ratio of Si to (Al+E) and varies from about 5 to about 12 and "z" is the mole ratio of O to (Al+E) and has a value determined by the equation:

$z=(m\cdot n+r\cdot p+3+4\cdot y)/2$ the material characterized in that it has at least two x-ray diffraction peaks, one at a d-spacing of 3.9±0.12 Å and one at 8.6±0.20 Å.

2. The process of claim 1 where the zeolite has a x-ray powder diffraction pattern which contains at least the d-spacing and relative intensities of one of Tables A to C.

3. The process of claim 1 where M is selected from the group consisting of lithium, cesium, sodium, potassium, strontium, barium, calcium, magnesium and mixtures thereof and R is a quaternary ammonium ion.

4. The process of claim 3 where the quaternary ammonium cation is selected from the group consisting of tetramethylammonium, tetraethylammonium, tetrapropylammonium, hexamethonium, diethyidimethylammonium, ethyltrimethylammonium and mixtures thereof.

5. The process of claim 3 where M is sodium and the quaternary ammonium cation is a mixture of tetraethylammonium and tetramethylammonium.

6. The process of claim 3 where M is lithium and the quaternary ammonium cation is a mixture of tetraethylammonium and tetramethylammonium.

7. The process of claim 1 where M is a mixture of an alkali metal and an alkaline earth metal and R is a quaternary ammonium cation.

8. The process of claim 7 where M is a mixture of lithium and strontium.

9. The process of claim 7 where the quaternary ammonium compound is selected from the group consisting of tetramethylammonium, tetraethylammonium, hexamethonium, tetrapropylammonium, diethyldimethylammonium, ethyltrimethylammonium and mixtures thereof.

10. The process of claim 9 where R is a mixture of tetramethylammonium and tetraethylammonium.

11. The process of claim 1 where "m" equals zero and R is a quaternary ammonium cation selected from the group consisting of tetramethylammonium, tetraethylammonium, hexamethonium, tetrapropylammonium, diethyldimethylammonium, ethyltrimethylammonium and mixtures thereof.

12. The process of claim 1 wherein the catalyst composite further comprises an inorganic-oxide binder.

13. The process of claim 12 wherein the inorganic-oxide binder comprises one or both of alumina and silica.

14. The process of claim 13 wherein the inorganic-oxide binder is alumina.

15. The process of claim 1 wherein the platinum-group metal component is present in an amount from about 0.01 to 5 mass-% on an elemental basis.

16. The process of claim 1 wherein ortho-xylene is recovered from one or both of the isomerized product and fresh feed mixture.

17. The process of claim 1 further comprising recovery of para-xylene by selective adsorption from the isomerized product and a fresh feed mixture.

18. The process of claim 1 where the isomerization conditions include a temperature of about 100° C. to about 500° C., a pressure from about 1 to about 50 atmospheres and a liquid hourly space velocity of about 0.5 to about 10 $hr^{-1}$.

19. The process of claim 1 where the hydrogen is present at a hydrogen to hydrocarbon ratio of about 0.5:1 to about 25:1.

* * * * *

UNITED STATES PATENT AND TRADEMARK OFFICE
CERTIFICATE OF CORRECTION

PATENT NO.    : 6,388,159 B1  
DATED         : May 14, 2002  
INVENTOR(S)   : Deng-Yang Jan et al.

Page 1 of 1

It is certified that error appears in the above-identified patent and that said Letters Patent is hereby corrected as shown below:

<u>Column 14,</u>  
Line 61, delete capital "X" and replace it with lowercase -- x --.

Signed and Sealed this

Twenty-fifth Day of June, 2002

*Attest:*

*Attesting Officer*

JAMES E. ROGAN  
*Director of the United States Patent and Trademark Office*